US012291690B2

(12) United States Patent
Stock et al.

(10) Patent No.: US 12,291,690 B2
(45) Date of Patent: May 6, 2025

(54) ETHERS AND ESTERS OF TERTIARY ALKANOLS FOR USE AS AROMA CHEMICALS

(71) Applicant: BASF SE, Ludwigshafen am Rhein (DE)

(72) Inventors: Christoph Stock, Ludwigshafen am Rhein (DE); Miriam Bru Roig, Ludwigshafen am Rhein (DE); Ralf Pelzer, Lampertheim (DE); Florian Garlichs, Lampertheim (DE); Manuel Danz, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 777 days.

(21) Appl. No.: 17/286,338

(22) PCT Filed: Oct. 15, 2019

(86) PCT No.: PCT/EP2019/077992
§ 371 (c)(1),
(2) Date: Apr. 16, 2021

(87) PCT Pub. No.: WO2020/079011
PCT Pub. Date: Apr. 23, 2020

(65) Prior Publication Data
US 2021/0388288 A1 Dec. 16, 2021

(30) Foreign Application Priority Data
Oct. 16, 2018 (EP) .................................. 18200677

(51) Int. Cl.
| | | |
|---|---|---|
| *C11B 9/00* | (2006.01) | |
| *C07C 43/04* | (2006.01) | |
| *C07C 43/15* | (2006.01) | |
| *C07C 69/007* | (2006.01) | |
| *C07C 69/14* | (2006.01) | |

(52) U.S. Cl.
CPC .......... *C11B 9/0015* (2013.01); *C07C 43/046* (2013.01); *C07C 43/15* (2013.01); *C07C 69/007* (2013.01); *C07C 69/14* (2013.01); *C11B 9/0019* (2013.01)

(58) Field of Classification Search
None
See application file for complete search history.

(56) References Cited

U.S. PATENT DOCUMENTS

| | | | |
|---|---|---|---|
| 4,168,248 A | 9/1979 | Kulka | |
| 9,434,676 B2 | 9/2016 | Beumer et al. | |
| 9,567,286 B2 | 2/2017 | Beumer et al. | |
| 2007/0219102 A1 | 9/2007 | Narula et al. | |
| 2015/0246868 A1 | 9/2015 | Beumer et al. | |

FOREIGN PATENT DOCUMENTS

| | | |
|---|---|---|
| CN | 104704093 A | 6/2015 |
| CN | 104704097 A | 6/2015 |
| EP | 1532092 B1 | 11/2008 |
| GB | 0652808 A | 5/1951 |
| GB | 1331204 A | 9/1973 |
| WO | 2014/056849 A1 | 4/2014 |
| WO | 2014/056850 A1 | 4/2014 |
| WO | 2014/056851 A2 | 4/2014 |
| WO | 2017/214446 A1 | 12/2017 |

OTHER PUBLICATIONS

Dong et al., "Palladium-catalyzed carbonylation of sec- and tert-alcohols", Catalysis, Angew. Chem. Int. Ed, 2017, 56, pp. 6203-6207. (Year: 2017).*
International Preliminary Report on Patentability received for PCT Patent Application No. PCT/EP2019/077992, mailed on Apr. 29, 2021, 9 pages.
International Search Report and Written Opinion received for PCT Patent Application No. PCT/EP2019/077992, mailed on Nov. 21, 2019, 11 pages.
Lidia M.P.C. Albuquerque et al.: "Kinetics and mechanism of solvolysis of 3-chloro-3-ethyl pentane in alcohols as solvents. Application of multi-parametric equations and factor analysis to the solvolytic reactions of tert-alkyl halides", Journal of Physical Organic Chemistry, vol. 14, 2001, pp. 139-145.
Raymond Quelet Et Jean D' Angelo: "No. 270—Action des organo-magnesiens sur les acetals alpha-ethyleniques. II.—Etude du comportement de quelques homologues et derives des acetals du propenal", Bulletin de la Societe Chimique de France, 1967, pp. 1503-1511.
U. I. Zahorszky: "Uber Quantitative Beziehungen Zwischen Fragmenten Uno Ihren Relativen Intensitaten im Massen-Spektrometer", Organic Mass Spectrometry, vol. 11, 1976, pp. 1254-1261.
STN Registry, Entered on Jan. 30, 2023, Registry No. 1659316-53-6, 872301-08-1, 121637-07-8, 62958-50-3, 35036-33-0, 16627-33-1, 16627-20-6, 5 pages.
Vinson et al., "Gold-Catalyzed, SN1-Type Reaction of Alcohols to Afford Ethers and Cbz-Protected Amines," Synlett, vol. 26, No. 06, Feb. 9, 2015, pp. 765-770.

(Continued)

*Primary Examiner* — Kyung S Chang
(74) *Attorney, Agent, or Firm* — Faegre Drinker Biddle & Reath LLP

(57) ABSTRACT

The present invention relates to the use of an ether or an ester of a tertiary alkanol or of mixtures of two or more ethers or esters of tertiary alkanols or of a stereoisomer thereof or of a mixture of two or more stereoisomers thereof as aroma-chemicals; to the use thereof for modifying the scent character of a fragranced composition; to an aroma chemical composition containing an ether or an ester of tertiary alkanol or of mixtures of two or more ethers or esters of tertiary alkanols or of a stereoisomer thereof or of a mixture of two or more stereoisomers thereof; and to a method of preparing a fragranced composition or for modifying the scent character of a fragranced composition. The invention further relates to specific ethers or esters of tertiary alkanols.

8 Claims, No Drawings

(56) References Cited

OTHER PUBLICATIONS

Leitereg et al., "Chemical and sensory data supporting the difference between the odors of the enantiomeric carvones", Journal of Agricultural and Food Chemistry, vol. 19, No. 4, Jul. 1, 1971, pp. 785-787.

Ohloff et al., "Stereochemistry-Activity Relationships in Olfaction. Odorants containing a proton donor/proton acceptor unit", Helvetica Chimica Acta, vol. 63, Issue 1, Jan. 23, 1980, pp. 76-94.

\* cited by examiner

ETHERS AND ESTERS OF TERTIARY ALKANOLS FOR USE AS AROMA CHEMICALS

CROSS-REFERENCE TO RELATED APPLICATIONS

This application is a national stage application (under 35 U.S.C. § 371) of PCT/EP2019/077992, filed Oct. 15, 2019, which claims benefit of European Application No. 18200677.5, filed Oct. 16, 2018, both of which are incorporated herein by reference in their entirety.

The present invention relates to the use of an ether or an ester of a tertiary alkanol or of mixtures of two or more ethers or esters of tertiary alkanols or of a stereoisomer thereof or of a mixture of two or more stereoisomers thereof as aroma chemicals; to the use thereof for modifying the scent character of a fragranced composition; to an aroma chemical composition containing an ether or an ester of a tertiary alkanol or of mixtures of two or more ethers or esters of tertiary alkanols or of a stereoisomer thereof or of a mixture of two or more stereoisomers thereof; and to a method of preparing a fragranced composition or for modifying the scent character of a fragranced composition.

The invention further relates to specific ethers or esters of tertiary alkanols.

TECHNICAL BACKGROUND

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resemble more expensive natural fragrances or which have novel and interesting organoleptic profiles.

Despite a large number of already existing synthetic aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other fragrances, a higher stability under certain application conditions, a higher extendability, a better substantivity, etc.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

U.S. Pat. No. 9,434,676 B2 describes the use of (1-ethyl-1,4,5-trimethyl-hex-4-enyl) acetate as flavor and fragrance material, as well as flavor and fragrance formulations comprising this compound.

US 2007/0219102 A1 describes lower ethers and esters of 3,7-dimethylnon-6-en-3-ol (1,2 dihydro-ethyl linalool) as well as fragrance formulations and fragrance products containing these compounds.

WO 2014/056851 describes the use of (1,5-dimethyl-1-vinyl-hexyl) acetate and derivatives thereof as flavor and fragrance material, as well as flavor and fragrance formulations comprising said compounds.

U.S. Pat. No. 9,567,286 B2 describes the use of tetrahydrolinalyl acetate ((1-ethyl-1,5-dimethyl-hexyl) acetate), 1,2-dihydrolinalyl acetate ((1-ethyl-1,5-dimethyl-hexyl) acetate) and derivatives thereof as flavor and fragrance material, as well as flavor and fragrance formulations comprising said compounds.

GB 1331204 describes the fragrance compound 1,1-diethylallyl 2-methylbutanoate and fragrance compositions comprising said compound.

Furthermore, linalyl acetate ((1,5-dimethyl-1-vinyl-hex-4-enyl) acetate) and tetrahydrolinalyl acetate ((1-ethyl-1,5-dimethyl-hexyl) acetate) are known to have a fresh fruity an floral odor.

It was an object of the present invention to provide new aroma chemicals. These should have pleasant organoleptic properties. It was a further object of the present invention to provide substances which can be used as an aroma chemical in ready-to-use compositions. In particular, odor-intensive substances having a pleasant odor are sought. Furthermore, they should be combinable with other aroma chemicals, allowing the creation of novel advantageous sensory profiles. In addition, these aroma chemicals should be obtainable from readily available starting materials, allowing their fast and economic manufacturing, and should be free of toxicological concerns.

It was a further particular object of the present invention to provide specific compounds or compound mixtures, which have a pronounced fruity, sweet and/or a floral odor note.

This object is achieved by the compound of formula (I) as shown below or mixtures thereof or stereoisomers thereof.

SUMMARY OF THE INVENTION

The invention relates to the use of a compound of the general formula (I)

(I)

wherein
R$^1$ is ethyl or ethenyl,
R$^2$ is C$_1$-C$_3$-alkyl,
R$^3$ is C$_2$-C$_4$-alkyl and
R$^4$ is C$_1$-C$_4$-alkyl or C$_1$-C$_4$-alkanoyl,
or of a mixture of two or more compounds of the general formula (I),
or of a stereoisomer thereof or of a mixture of two or more stereoisomers thereof, as an aroma chemical.

Another aspect of the invention is the use of a compound of formula (I) or a mixture of two or more compounds of formula (I) or a stereoisomer thereof or a mixture of two or more stereoisomers thereof for modifying the scent character of a fragranced composition, e.g. of a fragranced ready-to-use composition.

Yet another aspect of the invention is a composition comprising a compound of formula (I) or a mixture of two or more compounds of the general formula (I) or a stereoisomer thereof or a mixture of two or more stereoisomers thereof, and at least one further compound selected from the group consisting of further aroma chemicals different from compounds (I) and non-aroma chemical carriers, where the non-aroma chemical carrier is in particular selected from the group consisting of surfactants, oil components and solvents.

The invention also relates to a method for preparing a fragranced composition, e.g. a fragranced ready-to-use composition, or for modifying the scent character of a fragranced composition, e.g. of a fragranced ready-to-use composition, comprising incorporating a compound of formula (I) or a mixture of two or more compounds of the general formula (I) or a stereoisomer thereof or a mixture of two or more stereoisomers thereof into said composition.

Further, the invention relates to a compound of the general formula (I.a) or a stereoisomer thereof

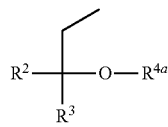

(I.a)

wherein
$R^2$ is $C_1$-$C_3$-alkyl,
$R^3$ is $C_2$-$C_4$-alkyl and
$R^{4a}$ is $C_2$-$C_4$-alkyl,
except for the compounds 3-ethoxy-3-ethyl-hexane, 3-ethoxy-3-methyl-pentane and 3-ethoxy-3-ethyl-pentane,
or
a compound of the general formula (I.b) or a stereoisomer thereof

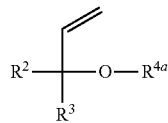

(I.b)

wherein
$R^2$ is $C_1$-$C_3$-alkyl,
$R^3$ is $C_2$-$C_4$-alkyl and
$R^{4a}$ is $C_2$-$C_4$-alkyl,
except for the compound 3-ethoxy-3-methylhept-1-ene and 3-ethoxy-3-methylpent-1-ene.

The invention also relates to a method for preparing a compound of formulae (I.a) or (I.b) or a mixture of two or more compounds of formulae (I.a) and/or (I.b) or a stereoisomer thereof or a mixture of two or more stereoisomers thereof.

The compounds of formula (I) as well as mixtures of two or more compounds of formula (I), their stereoisomers and the mixtures of their stereoisomers possess advantageous organoleptic properties, in particular a pleasant odor. Therefore, they can be favorably used as an aroma chemical for example in perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions, crop protection compositions and other ready-to-use compositions.

By virtue of their physical properties, the compounds of formula (I) as well as mixtures of two or more compounds of formula (I), their stereoisomers and the mixtures of their stereoisomers have particularly good, virtually universal solvent properties for and in aroma chemicals and other customary ingredients in fragranced compositions such as, in particular, perfume compositions. Therefore, the compounds of formula (I) as well as mixtures of two or more compounds of formula (I), their stereoisomers and the mixtures of their stereoisomers are favorably combinable with aroma chemicals, allowing, in particular, the creation of aroma compositions, in particular fragranced compositions having novel advantageous sensory profiles.

Furthermore, the compounds of formula (I) as well as mixtures of two or more compounds of formula (I), their stereoisomers and the mixtures of their stereoisomers can be produced in good yields and purities by a simple synthesis which generally requires only one step, starting from readily available starting compounds. Thus, the compounds of formula (I) as well as mixtures of two or more compounds of formula (I), their stereoisomers and the mixtures of their stereoisomers can be produced in large scales and in a simple and cost-efficient manner.

DETAILED DESCRIPTION OF THE INVENTION

In mixtures of two or more compounds of the formula (I) the two or more different compounds (I) differ in the definition of at least one of the radicals $R^1$, $R^2$, $R^3$ and $R^4$.

In the context of the present invention, the term "alkyl" as used herein refers to a linear or branched saturated hydrocarbon radicals having 1 to 3 ("$C_1$-$C_3$-alkyl"), 1 to 4 ("$C_1$-$C_4$-alkyl"), 2 to 4 ("$C_2$-$C_4$-alkyl") or 2 to 5 ("$C_2$-$C_5$-alkyl") carbon atoms. $C_1$-$C_3$-alkyl is methyl, ethyl, propyl and isopropyl. $C_1$-$C_4$-alkyl is additionally n-butyl, 1-methylpropyl (sec-butyl), 2-methylpropyl (isobutyl) or 1,1-dimethylethyl (tert-butyl). $C_2$-$C_5$-alkyl is for example ethyl, propyl and isopropyl, n-butyl, 1-methylpropyl (sec-butyl), 2-methylpropyl (isobutyl), 1,1-dimethylethyl (tert-butyl), n-pentyl, 1-methylbutyl, 2-methylbutyl, 3-methylbutyl, 1-ethylpropyl, 1,3-dimethylpropyl, 2,3-dimethylpropyl, 3,3-dimethylpropyl and the like.

In the context of the present invention, the term "$C_1$-$C_5$-alkanoyl" denotes a hydrogen atom or a $C_1$-$C_4$-alkyl group, as defined above, attached via a carbonyl [(C=O)] group to the remainder of the molecule. The term "$C_2$-$C_5$-alkanoyl" denotes a $C_1$-$C_4$-alkyl group, as defined above, attached via a carbonyl [(C=O)] group to the remainder of the molecule. $C_1$-$C_5$-alkanoyl is formyl, methylcarbonyl, ethylcarbonyl, n-propylcarbonyl, isopropylcarbonyl, n-butylcarbonyl, 1-methylpropylcarbonyl, 2-methylpropylcarbonyl or 1,1-dimethylethylcarbonyl.

The term "stereoisomers" encompasses optical isomers, such as enantiomers or diastereomers, the latter existing due to more than one stereogenic center in the molecule. The compounds of the formula (I) may have one stereogenic center, namely the α-carbon atom carrying the radicals $R^1$, $R^2$ and $R^3$, in case the radicals $R^1$, $R^2$ and $R^3$ have different meanings. Furthermore, the radical $R^3$ may also have a stereogenic center if $R^3$ is selected from 1-methylpropyl. Furthermore, the radical Ra may also have a stereogenic center, for example if $R^4$ is selected from 1-methylpropyl or 1-methylpropylcarbonyl. The invention provides both the pure enantiomers or diastereomers and mixtures thereof and the use according to the invention of the pure enantiomers or pure diastereomers of the compound (I) or mixtures thereof.

In the present context, the term "compound (I)" or "compound of formula (I)", when not defined as a specific stereoisomer or a specific mixture of stereoisomers, refers to the form of the compound as it is obtained in a non-stereoselective method used for its production. The term is however also used if it is not necessary or not possible to specify in more detail the stereochemistry of the compound (I).

Preferably, $R^1$ is ethyl.
Preferably, $R^2$ is methyl or ethyl, in particular ethyl.
Preferably, $R^3$ is $C_2$-$C_3$-alkyl, in particular ethyl or isopropyl.

A first preferred embodiment of the present invention relates to the use of a compound of the general formula (I)

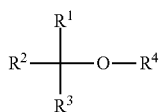

(I)

wherein
$R^1$ is ethyl or ethenyl,
$R^2$ is $C_1$-$C_3$-alkyl,
$R^3$ is $C_2$-$C_4$-alkyl and
$R^4$ is $C_1$-$C_4$-alkyl,
or of a mixture of two or more compounds of the general formula (I),
or of a stereoisomer thereof or of a mixture of two or more stereoisomers thereof, as an aroma chemical.

Preferably, in compounds (1) of this first preferred embodiment,
$R^1$ is ethyl or ethenyl,
$R^2$ is methyl or ethyl,
$R^3$ is $C_2$-$C_4$-alkyl and
$R^4$ is $C_1$-$C_4$-alkyl, in particular $C_1$-$C_3$-alkyl.

More preferably, in compounds (I) of this first preferred embodiment,
$R^1$ is ethyl or ethenyl,
$R^2$ is methyl or ethyl,
$R^3$ is $C_2$-$C_4$-alkyl and
$R^4$ is $C_1$-$C_3$-alkyl, in particular methyl or ethyl.

Even more preferably, in compounds (I) of this first preferred embodiment,
$R^1$ is ethyl or ethenyl,
$R^2$ is methyl or ethyl,
$R^3$ is $C_2$-$C_3$-alkyl and
$R^4$ is $C_1$-$C_3$-alkyl, in particular methyl or ethyl.

In particular, in compounds (I) of this first preferred embodiment,
$R^1$ is ethyl or ethenyl,
$R^2$ is methyl or ethyl,
$R^3$ is ethyl or isopropyl and
$R^4$ is methyl or ethyl, in particular methyl.

A second preferred embodiment of the present invention relates to the use of a compound of the general formula (I)

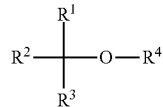

(I)

wherein
$R^1$ is ethyl or ethenyl,
$R^2$ is $C_1$-$C_3$-alkyl,
$R^3$ is $C_2$-$C_4$-alkyl and
$R^4$ is $C_2$-$C_4$-alkyl,
or of a mixture of two or more compounds of the general formula (I),
or of a stereoisomer thereof or of a mixture of two or more stereoisomers thereof, as an aroma chemical.

Preferably, in compounds (I) of this second preferred embodiment,
$R^1$ is ethyl or ethenyl,
$R^2$ is methyl or ethyl,
$R^3$ is $C_2$-$C_4$-alkyl and
$R^4$ is $C_2$-$C_4$-alkyl, in particular $C_2$-$C_3$-alkyl.

More preferably, in compounds (I) of this second preferred embodiment,
$R^1$ is ethyl or ethenyl,
$R^2$ is methyl or ethyl,
$R^3$ is $C_2$-$C_4$-alkyl and
$R^4$ is $C_2$-$C_3$-alkyl, in particular ethyl.

In particular, in compounds (I) of this second preferred embodiment,
$R^1$ is ethyl,
$R^2$ is methyl or ethyl,
$R^3$ is ethyl, n-propyl or isopropyl and
$R^4$ is $C_2$-$C_3$-alkyl, in particular ethyl.

A third preferred embodiment of the present invention relates to the use of a compound of the general formula (I)

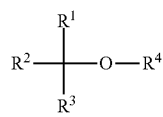

(I)

wherein
$R^1$ is ethyl or ethenyl,
$R^2$ is $C_1$-$C_3$-alkyl,
$R^3$ is $C_2$-$C_4$-alkyl and
$R^4$ is $C_1$-$C_4$-alkanoyl,
or of a mixture of two or more compounds of the general formula (I),
or of a stereoisomer thereof or of a mixture of two or more stereoisomers thereof, as an aroma chemical.

Preferably, in compounds (I) of this third preferred embodiment,
$R^1$ is ethyl or ethenyl,
$R^2$ is $C_1$-$C_3$-alkyl,
$R^3$ is $C_2$-$C_4$-alkyl and
$R^4$ is $C_2$-$C_3$-alkanoyl.

More preferably, in compounds (I) of this third preferred embodiment,
$R^1$ is ethyl or ethenyl,
$R^2$ is methyl or ethyl,
$R^3$ is $C_2$-$C_4$-alkyl and
$R^4$ is $C_2$-$C_3$-alkanoyl.

Even more preferably, in compounds (I) of this third preferred embodiment,
$R^1$ is ethyl or ethenyl,
$R^2$ is methyl or ethyl,
$R^3$ is $C_2$-$C_3$-alkyl and
$R^4$ is $C_2$-$C_3$-alkanoyl.

In particular, in compounds (I) of this third preferred embodiment,
$R^1$ is ethyl or ethenyl,
$R^2$ is methyl or ethyl,
$R^3$ is ethyl or isopropyl and
$R^4$ is $C_2$-$C_3$-alkanoyl, in particular acetyl or propionyl.

Especially, in compounds (I) of this third preferred embodiment,
$R^1$ is ethyl,
$R^2$ is methyl or ethyl,
$R^3$ is ethyl or isopropyl and
$R^4$ is acetyl or propionyl.

A fourth preferred embodiment of the present invention relates to the use of a compound of the general formula (I)

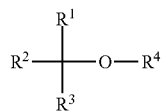

(I)

wherein
$R^1$ is ethyl or ethenyl,
$R^2$ is $C_1$-$C_3$-alkyl,
$R^3$ is $C_2$-$C_4$-alkyl and
$R^4$ is $C_2$-$C_4$-alkanoyl,
or of a mixture of two or more compounds of the general formula (I),
or of a stereoisomer thereof or of a mixture of two or more stereoisomers thereof, as an aroma chemical.

Preferably, in compounds (I) of this fourth preferred embodiment,
$R^1$ is ethyl or ethenyl,
$R^2$ is $C_1$-$C_3$-alkyl,
$R^3$ is $C_2$-$C_4$-alkyl and
$R^4$ $C_3$-$C_4$-alkanoyl.

More preferably, in compounds (I) of this fourth preferred embodiment,
$R^1$ is ethyl or ethenyl,
$R^2$ is methyl or ethyl,
$R^3$ is $C_2$-$C_4$-alkyl and
$R^4$ $C_3$-$C_4$-alkanoyl.

In particular, in compounds (I) of this fourth preferred embodiment,
$R^1$ is ethyl or ethenyl,
$R^2$ is methyl or ethyl,
$R^3$ is ethyl, n-propyl or isopropyl and
$R^4$ is $C_3$-$C_5$-alkanoyl, in particular $C_3$-$C_4$-alkanoyl.

Especially, in compounds (I) of this fourth preferred embodiment,
$R^1$ is ethyl or ethenyl,
$R^2$ is methyl or ethyl,
$R^3$ is ethyl or isopropyl and
$R^4$ is $C_3$-$C_4$-alkanoyl, in particular propionyl.

Preferable Compounds (I) that can be Advantageously Used as Aroma Chemicals are for Example
3-methoxy-2,3-dimethyl-pentane,
3-ethoxy-2,3-dimethyl-pentane,
3-ethyl-3-methoxy-pentane,
3-ethyl-3-ethoxy-pentane,
3-methoxy-3,4-dimethyl-pent-1-ene,
3-ethoxy-3,4-dimethyl-pent-1-ene,
3-ethyl-3-methoxy-pent-1-ene,
3-ethyl-3-ethoxy-pent-1-ene,
(1-ethyl-1,2-dimethyl-propyl) acetate,
(1-ethyl-1,2-dimethyl-propyl) propanoate,
(1-isopropyl-1-methyl-allyl) acetate,
(1-isopropyl-1-methyl-allyl) propanoate,
1,1-diethylpropyl acetate,
1,1-diethylpropyl propanoate,
1,1-diethylallyl acetate,
1,1-diethylallyl propanoate, or
mixtures of the aforesaid preferable compounds (I).

More Preferable Compounds (I) that can be Advantageously Used as Aroma Chemicals are for Example
3-methoxy-2,3-dimethyl-pentane,
3-ethyl-3-methoxy-pentane,
3-ethyl-3-methoxy-pent-1-ene,
(1-ethyl-1,2-dimethyl-propyl) acetate,
(1-isopropyl-1-methyl-allyl) acetate,
1,1-diethylpropyl acetate,
1,1-diethylpropyl propanoate,
1,1-diethylallyl acetate, or
mixtures of the aforesaid preferable compounds (I).

Particularly Preferable Compounds (I) that can be Advantageously Used as Aroma Chemicals are for Example
(1-ethyl-1,2-dimethyl-propyl) acetate,
1,1-diethylpropyl acetate,
1,1-diethylallyl acetate,
1,1-diethylpropyl propanoate,
3-methoxy-2,3-dimethyl-pentane,
3-ethyl-3-methoxy-pentane, or
mixtures of the aforesaid compounds (I).

A further preferred embodiment of the present invention relates to the use of a mixture of two or more compounds of formula (I), as defined herein, as an aroma chemical.

As indicated above, the two or more different compounds (I) in these mixtures differ in the definition of at least one of the radicals $R^1$, $R^2$, $R^3$ and $R^4$. Preferably, the two or more different compounds (1) in these mixtures differ in the definition of at least one of the radicals $R^1$ and $R^4$. A particular embodiment relates to the use of a mixture of two compounds of formula (I), as defined herein, which differ in the definition of the radical $R^1$, as an aroma chemical.

Preferable Mixtures are for Example
mixtures of 3-ethyl-3-methoxy-pentane and 3-ethyl-3-methoxy-pent-1-ene,
mixtures of 1,1-diethylpropyl acetate and 1,1-diethylallyl acetate, and
mixtures of (1-ethyl-1,2-dimethyl-propyl) acetate and (1-isopropyl-1-methyl-allyl) acetate.

The compounds of formula (I) as well as the mixtures of two or more compounds of formula (I), the stereoisomers thereof and the mixtures of stereoisomers thereof, as defined above, are useful as aroma chemicals.

In the context of the present invention, the term "aroma" refers to a sensory property and comprises an odor and/or a flavor.

The term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression.

The term "aroma profile" denotes the overall aroma impression of an aroma chemical and is composed of the individual aroma impressions of an aroma chemical.

The term "aroma composition" or "aroma chemical composition", as used herein, refers to a composition which induces an aroma. The term aroma composition comprises "odor composition" and/or "flavor composition". An odor composition being a composition, which predominately induces an odor impression, a flavor composition being a composition, which predominantly induces a taste impression.

The term odor composition comprises "fragrance composition" or "scent composition" (used interchangeably herein), which predominately induce an odor impression which is generally felt as pleasant.

The terms "compound" and "substance" are used synonymously throughout the invention.

The term "substantivity" describes the interaction of an aroma chemical with a surface, such as for example the skin or a textile, especially after subsequent treatment of the surface, such as for example washing. The substantivity can for example be determined by washing a textile with a textile detergent composition comprising the aroma chemical and subsequent olfactory evaluation of the textile directly after washing (wet textile) as well as evaluation of the dry textile after prolonged storage.

The term "stability" describes the behavior of an aroma chemical upon contact with oxygen, light and/or other substances. An aroma chemical with high stability maintains its aroma profile over a long period in time, preferably in a large variety of compositions and under various storage conditions.

The term "sensory impression", as used herein, refers to an odor impression and/or a taste impression, in particular an odor impression.

"Pleasant odor", "pleasant odor impression", "pleasant odiferous properties" are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations. The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the $ppb/m^3$ range.

Preferably, the compounds of formula (I) as well as the mixtures of two or more compounds of formula (I), the stereoisomers thereof and the mixtures of stereoisomers thereof, as defined above, are used as a fragrance.

In particular, (1-ethyl-1,2-dimethyl-propyl) acetate is used to impart a fruity, galbanum, camphorous, rooty and earthy note; or is used to produce a scent with a fruity, galbanum, camphorous, rooty and earthy note.

In particular, 1,1-diethylpropyl acetate is used to impart a fir needle, camphor, fresh, and natural note; or is used to produce a scent with a fir needle, camphor, fresh and natural note.

In particular, a mixture comprising 70% by weight of 1,1-diethylallyl acetate and 25% by weight of 1,1-diethylpropyl acetate is used to impart a floral, honey and dried fruit note; or is used to produce a scent with a floral, honey and dried fruit note.

In particular, 1,1-diethylpropyl propanoate is used to impart a fruity, camphorous, sweet, cherry and solvent note; or are used to produce a scent with a fruity, camphorous, sweet, cherry and solvent note.

In particular, 3-methoxy-2,3-dimethyl-pentane is used to impart an ethereal, sweet, mouldy, hay, chocolate, eucalyptus and leafy note; or is used to produce a scent with an ethereal, sweet, mouldy, hay, chocolate, eucalyptus and leafy note.

In particular, 3-ethyl-3-methoxy-pentane is used to impart a mouldy, woody, cedarwood and galbanum note; or is used to produce a scent with a mouldy, woody, cedarwood, galbanum note.

In particular, a mixture comprising 85% by weight of (1-isopropyl-1-methyl-allyl) acetate and 10% by weight of (1-ethyl-1,2-dimethyl-propyl) acetate is used to impart a lovage, sweet, woody and fruity note; or is used to produce a scent with a lovage, sweet, woody and fruity note.

In particular, a mixture comprising 90% by weight of 3-ethyl-3-methoxy-pent-1-ene and 10% by weight of 3-ethyl-3-methoxy-pentane is used to impart an animalic, blackcurrant, sweet and technical note; or is used to produce a scent with an animalic, blackcurrant, sweet and technical note.

The compounds of formula (I) as well as the mixtures of two or more compounds of formula (I), the stereoisomers thereof and the mixtures of stereoisomers thereof, as defined above, are generally used in a ready-to-use composition, in particular in a fragranced ready-to-use composition. "Fragranced ready-to-use composition", as used herein, refers to a ready-to-use composition which predominately induces a pleasant odor impression.

Fragranced ready-to-use compositions are for example compositions used in personal care, in home care, in industrial applications as well as compositions used in other applications, such as pharmaceutical compositions or crop protection compositions.

Preferably, the compounds of formula (I) as well as the mixtures of two or more compounds of formula (I), the stereoisomers thereof and the mixtures of stereoisomers thereof are used in a composition selected from the group consisting of perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions. The compounds of formula (I) as well as the mixtures of two or more compounds of formula (I), the stereoisomers thereof and the mixtures of stereoisomers thereof are used as an aroma chemical, preferably as a fragrance, in the above compositions.

In particular, (1-ethyl-1,2-dimethyl-propyl) acetate is used to impart a fruity, galbanum, camphorous, rooty and earthy note to the above-listed compositions.

In particular, 1,1-diethylpropyl acetate is used to impart a fir needle, camphor, fresh, and natural note to the above-listed compositions.

In particular, a mixture comprising 70% by weight of 1,1-diethylallyl acetate and 25% by weight of 1,1-diethylpropyl acetate is used to impart a floral, honey and dried fruit note to the above-listed compositions.

In particular, 1,1-diethylpropyl propanoate is used to impart a fruity, camphorous, sweet, cherry and solvent note to the above-listed compositions.

In particular, 3-methoxy-2,3-dimethyl-pentane is used to impart an ethereal, sweet, mouldy, hay, chocolate, eucalyptus and leafy note to the above-listed compositions.

In particular, 3-ethyl-3-methoxy-pentane is used to impart a mouldy, woody, cedarwood and galbanum note to the above-listed compositions.

In particular, a mixture comprising 85% by weight of (1-isopropyl-1-methyl-allyl) acetate and 10% by weight of (1-ethyl-1,2-dimethyl-propyl) acetate is used to impart a lovage, sweet, woody and fruity note to the above-listed compositions.

In particular, a mixture comprising 90% by weight of 3-ethyl-3-methoxy-pent-1-ene and 10% by weight of 3-ethyl-3-methoxy-pentane is used to impart an animalic, blackcurrant, sweet and technical note to the above-listed compositions.

Details to the above-listed compositions are given below.

Accordingly, another aspect of the invention relates to the use of a compounds of formula (I) or mixtures of two or more compounds of formula (I), or a stereoisomer thereof or a mixtures of stereoisomers thereof for modifying the scent character of a fragranced composition.

In addition to the olfactory properties, the compounds of formula (I) as well as the mixtures of two or more compounds of formula (I), the stereoisomers thereof and the mixtures of stereoisomers thereof exhibit advantageous secondary properties.

For example, they can provide better sensory profiles as a result of synergistic effects with other fragrances, which means that they can provide a booster effect for other fragrances. They can therefore be used as boosters for other fragrances.

Accordingly, another aspect of the invention relates to the use of a compound of formula (I) or mixtures of two or more compounds of formula (I), or a stereoisomer thereof or a mixtures of stereoisomers thereof as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster. Booster effects are particularly desired when top-notecharacterized applications are required, in which the odor impression is to be conveyed particularly quickly and intensively, for example in deodorants, air fresheners or in the taste sector in chewing gums.

To achieve such a booster effect, the compounds of formula (I) or the mixture of two or more compounds of formula (I), or the stereoisomers thereof or the mixtures of stereoisomers thereof are generally used in an overall amount of 0.1-20% by weight, preferably in an amount of 0.5 to 5% by weight, in particular in an amount of from 0.6 to 3% by weight, based on the total weight of the fragrance mixture.

Furthermore, the compounds of formula (I) as well as the mixtures of two or more compounds of formula (I), the stereoisomers thereof and the mixtures of stereoisomers thereof can have further positive effects on the composition in which they are used. For example, they can enhance the overall performance of the composition into which they are incorporated, such as the stability, e.g. the formulation stability, the extendability or the substantivity of the composition.

In another aspect, the present invention relates to an aroma chemical composition comprising the compounds of formula (I) or a mixture of two or more compounds of formula (I), or a stereoisomer thereof or a mixture of stereoisomers thereof. The term "aroma chemical composition", as used herein, refers to a composition which induces a pleasant odor impression.

Preferably, the Aroma Chemical Composition Comprises
   a compound of formula (I) or a mixture of two or more compounds of the general formula (I) or a stereoisomer thereof or a mixture of two or more stereoisomers thereof; and
   at least one further aroma chemical and/or a non-aroma chemical carrier, where the non-aroma chemical carrier is in particular selected from the group consisting of surfactants, oil components and solvents.

The further aroma chemical is of course different from the compounds of formula (I) or its stereoisomers or mixtures of its stereoisomers.

By virtue of their physical properties, the compounds of formula (I) as well as the mixtures of two or more compounds of formula (I), the stereoisomers thereof and the mixtures of stereoisomers thereof have particularly good, virtually universal solvent properties for and in aroma chemicals and other customary ingredients in fragranced compositions such as, in particular, perfume compositions. Therefore, they are well combinable with aroma chemicals, allowing, in particular, the creation of aroma compositions, in particular fragrance compositions, having novel advantageous sensory profiles. Furthermore, as already explained above, they can provide a booster effect for other fragrances.

Accordingly, in one preferred embodiment, the aroma chemical composition comprises a compound of formula (I) or a mixture of two or more compounds of formula (I), a stereoisomer thereof or a mixture of stereoisomers thereof, as defined above; and at least one further aroma chemical.

The further aroma chemical can for example be one, preferably 2, 3, 4, 5, 6, 7, 8 or further aroma chemicals, selected from the group consisting of:
   Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lysmeral[4]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyra[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melona[2]), borneol, 3-(3-isopropylphenyl)butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone[9]), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]), 3-(4-tert-butylphenyl)-propanal (Bourgeonal[4]), ethyl 2-methylpentanoate (Manzanate[4]), ethoxymethoxycyclododecane (Amberwood[1]), 2,4-dimethyl-4,4a,5,9b-tetrahydroindeno[1,2-d][1,3]dioxine (Magnolan[1]), (2-tert-butylcyclohexyl) acetate (Verdox[3]) and 3-[5,5,6-trimethylbicyclo[2.2.1]hept-2-yl]cyclohexan-1-ol (Sandela[4]). Within the context of the present invention, the aforementioned aroma chemical(s) are accordingly preferably combined with the compound of formula (I) or a mixture of two or more compounds of formula (I), or a stereoisomer thereof or a mixture of stereoisomers thereof, as defined above.

Where trade names are given above, these refer to the following sources:
[1] trade name of Symrise GmbH, Germany;
[2] trade name of Givaudan AG, Switzerland;
[3] trade name of International Flavors & Fragrances Inc., USA;
[4] trade name of BASF SE;
[9] trade name of Firmenich S.A., Switzerland;
[10] trade name of PFW Aroma Chemicals B.V., the Netherlands.

A preferred embodiment of the invention relates to a composition comprising the compound of formula (I) or a mixture of two or more compounds of formula (I), or a stereoisomer thereof or a mixture of stereoisomers thereof, as defined above, and at least one further aroma chemical selected from the group consisting of methyl benzoate, benzyl acetate, geranyl acetate, 2-isobutyl-4-methyltetrahydro-2H-pyran-4-ol, linalool, 2-isobutyl-4-methyltetrahydro-2H-pyran-4-ol and methyl benzoate.

Further aroma chemicals with which the compound of formula (I) or a mixture of two or more compounds of formula (I), or a stereoisomer thereof or a mixture of stereoisomers thereof, as defined above, can be combined, e.g. to give a composition according to the invention, can be found e.g. in S. Arctander, Perfume and Flavor Chemicals, Vol. I and II, Montclair, N. J., 1969, self-published or K. Bauer, D. Garbe and H. Surburg, Common Fragrance and Flavor Materials, 4th Ed., WileyVCH, Weinheim 2001. Specifically, mention may be made of:
- extracts from natural raw materials such as essential oils, concretes, absolutes, resins, resinoids, balsams, tinctures such as e.g.
- ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;
- individual fragrances from the group of hydrocarbons, such as e.g. 3-carene; alphapinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;
- the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate;

methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethylacetals of geranial, neral, 7-hydroxy-3,7-dimethyloctanal; the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alphasinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro- 2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate; the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The at least one non-aroma chemical carrier can be a compound, a mixture of compounds or other additives, which have no or no noteworthy sensory properties. Typically, the at least one non-aroma chemical carrier, if present in the aroma chemical compositions according to the present invention, is a compound, a mixture of compounds or other additives, which have no or no noteworthy sensory properties. The non-aroma chemical carrier serves for the dilution and/or the fixing of the aroma chemical(s), i.e. the compounds of formula (I) and optionally one or more further aroma chemical different from compounds (I), as defined above, comprised in the aroma chemical composition.

Suitable carrier materials can be liquid or oil-like carrier materials as well as wax-like or solid carrier materials.

Preferably, the non-aroma chemical carrier, if present in the compositions according to the present invention, is selected from the group consisting of surfactants, oil components and solvents.

Accordingly, a further aspect of the invention is directed to a composition comprising the compound of formula (I) or a mixture of two or more compounds of formula (I), or a stereoisomer thereof or a mixture of stereoisomers thereof, as defined above, and at least one component selected from the group consisting of surfactants, emollients (oil component) and solvents.

One embodiment of the invention is directed to a composition comprising the compound of formula (I) or a mixture of two or more compounds of formula (I), or a stereoisomer thereof or a mixture of stereoisomers thereof, as defined above, and at least one solvent.

In the context of the present invention, a "solvent" serves for the dilution of the compound of formula (I) or a mixture of two or more compounds of formula (I), or a stereoisomer thereof or a mixture of stereoisomers thereof, as defined above, to be used according to the invention and/or any further component of the composition without having its own aroma.

The one or more solvent(s) can be present in the composition from 0.01 to 99% by weight based on the composition. In a preferred embodiment of the invention, the composition comprises 0.1 to 90 weight %, preferably 0.5 to 80 weight % of solvent(s) based on the composition. The amount of solvent(s) can be chosen depending on the composition. In one embodiment of the invention, the composition comprises 0.05 to 10 weight %, preferably 0.1 to 5 weight %, more preferably 0.2 to 3 weight % based on the composition. In one embodiment of the invention, the composition comprises 20 to 70 weight %, preferably 25 to 50 weight % of solvent(s) based on the composition.

Suitable solvents are for example ethanol, isopropanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Preferred solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, the compounds of formula (I) as well as the mixtures of two or more compounds of formula (I), the stereoisomers thereof and the mixtures of stereoisomers thereof are suitable for use in surfactant-containing compositions. According to their characteristic scent profiles, they can especially be used for the perfuming of surfactant-containing compositions such as, for example, cleaners (in particular laundry care products and all-purpose cleaners).

One embodiment of the invention is therefore directed to a composition comprising the compound of formula (I) or a mixture of two or more compounds of formula (I), or a stereoisomer thereof or a mixture of stereoisomers thereof, as defined above, and at least one surfactant.

The surfactant(s) may be selected from anionic, nonionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one —COOH— or —$SO_3H$—group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trim ethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants.

"Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising the compound of formula (I) or a mixture of two or more compounds of formula (I), or a stereoisomer thereof or a mixture of stereoisomers thereof, as defined above, and at least one oil component.

The oil components are typically present in a total quantity of 0.1 to 80, preferably 0.5 to 70, more preferably 1 to 60, even more preferably 1 to 50% by weight, in particular 1 to 40% by weight, more particularly 5 to 25% by weight and specifically 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl ole-ate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkyl-hydroxycarboxylic acids with linear or branched $C_6$-$C_{22}$-fatty alcohols, more especially dioctyl malate, esters of linear and/or branched fatty acids with polyhydric alcohols (for example propylene glycol, dimer dial or trimer triol), triglycerides based on $C_6$-$C_{10}$-fatty acids, liquid mono-, di- and triglyceride mixtures based on $C_6$-$C_{18}$-fatty acids, esters of $C_6$-$C_{22}$-fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol© CC), Guerbet carbonates based on fatty alcohols containing 6 to 18 and preferably 8 to 10 carbon atoms, esters of benzoic acid with linear and/or branched $C_6$ to $C_{22}$-alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

Another embodiment of the invention is directed to a composition comprising the compound of formula (I) or a mixture of two or more compounds of formula (I), or a stereoisomer thereof or a mixture of stereoisomers thereof, as defined above, and at least one anti-oxidant.

Anti-oxidants are able to inhibit or prevent the undesired changes in the compositions to be protected caused by oxygen effects and other oxidative processes. The effect of the anti-oxidants consists in most cases in them acting as free-radical scavengers for the free radicals which arise during autoxidation.

Anti-oxidants can for example be selected from the group consisting of
amino acids (for example glycine, alanine, arginine, serine, threonine, histidine, tyrosine, tryptophan) and derivatives thereof,
imidazoles (e.g. urocanic acid) and derivatives thereof,
peptides, such as D,L-carnosine, D-carnosine, L-carnosine (=β-Alanyl-L-histidin) and derivatives thereof,
carotenoids, carotenes (e.g. alpha-carotene, beta-carotene, lycopene, lutein) or derivatives thereof,
chlorogenic acid and derivatives thereof,
lipoic acid and derivatives thereof (for example dihydrolipoic acid),
auro-thioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof,
dilauryl thiodipropionate, distearyl thiodipropionate, thiodipropionic acid and derivatives thereof (esters, ethers, peptides, lipids, nucleotides, nucleosides and salts),
sulfoximine compounds (for example buthionine sulfoximines, homocysteine sulfoximine, buthionine sulfones, penta-, hexa-, heptathionine sulfoximine),
(metal) chelating agents (e.g. alpha-hydroxy fatty acids, palmitic acid, phytic acid, lactoferrin),
alpha-hydroxy acids (for example citric acid, lactic acid, malic acid),
humic acid, bile acid, bile extracts, bilirubin, biliverdin, boldin (=alkaloid from the plant Peumus boldus, boldo extract,
EDTA, EGTA and derivatives thereof,
unsaturated fatty acids and derivatives thereof (e.g. gamma-linolenic acid, linoleic acid, oleic acid),
folic acid and derivatives thereof,
ubiquinone and ubiquinol and derivatives thereof,
vitamin C and derivatives (for example ascorbyl palmitate, Mg ascorbyl phosphate, ascorbyl acetate),
tocopherols and derivatives (for example vitamin E acetate),
vitamin A and derivatives (for example vitamin A palmitate),
coniferyl benzoate of gum benzoin, rutic acid and derivatives thereof, alpha-glycosylrutin, ferulic acid, furfurylideneglucitol,
butylhydroxytoluene (BHT), butylhydroxyanisole (BHA),
nordihydroguaiacic acid, nordihydroguaiaretic acid, trihydroxybutyrophenone, uric acid and derivatives thereof, mannose and derivatives thereof,
superoxide dismutase,
zinc and derivatives thereof (for example ZnO, $ZnSO_4$), selenium and derivatives thereof (for example selenomethionine) and stilbenes and derivatives thereof (e.g. stilbene oxide, trans-stilbene oxide).

In a preferred embodiment, the anti-oxidant is selected from the group consisting of pentaerythrityl, tetra-di-t-butyl hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.

The compositions according to the invention can comprise the anti-oxidants in an amount of 0.001 to 25 wt.-%, preferably 0.005 to 10 wt.-%, preferably 0.01 to 8 wt. %, preferably 0.025 to 7 wt.-%, preferably 0.05 to 5 wt.-%, based on the total weight of the composition.

The compound of formula (I) or a mixture of two or more compounds of formula (I), or a stereoisomer thereof or a mixture of stereoisomers thereof, as defined above, can also be used together with deodorizing compositions.

Deodorizing compositions (deodorants and antiperspirants) counteract, mask or eliminate body odors. Body odors are formed through the action of skin bacteria on apocrine perspiration which results in the formation of unpleasant-smelling degradation products.

Another embodiment of the invention is therefore directed to a composition comprising the compound of formula (I) or a mixture of two or more compounds of formula (I), or a stereoisomer thereof or a mixture of stereoisomers thereof, as defined above, and at least one deodorant-active agent.

In a preferred embodiment of the invention, the at least one deodorant-active agent is selected from the groups consisting of anti-perspirants, esterase inhibitors and anti-bacterial agents.

Suitable antiperspirants can be selected from the group consisting of salts of aluminium, zirconium or zinc. Examples are aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Aluminium chlorohydrate, aluminium zirconium tetrachlorohydrate, aluminium zirconium pentachlorohydrate and complex compounds thereof are preferably used.

In a preferred embodiment of the invention the compositions comprise at least one antiperspirant selected from the group consisting aluminium chloride, aluminium chlorohydrate, aluminium dichlorohydrate, aluminium sesquichlorohydrate, aluminium hydroxyallantoinate, aluminium chloride tartrate, aluminium zirconium trichlorohydrate, aluminium zirconium tetrachlorohydrate and aluminium zirconium pentachlorohydrate.

The compositions according to the invention can comprise the antiperspirants in an amount of 1 to 50, preferably 5 to 30 and more particularly 10 to 25 wt.-%, based on the solids content of the composition.

Where perspiration is present in the underarm region, extracellular enzymes-esterases, mainly proteases and/or lipases are formed by bacteria and split the esters present in the perspiration, releasing odors in the process. Suitable esterase inhibitors are for example trialkyl citrates, such as trimethyl citrate, tripropyl citrate, triisopropyl citrate, tributyl citrate and, in particular, triethyl citrate. Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

In a preferred embodiment of the invention the compositions comprise at least one esterase inhibitor selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, tartaric acid diethyl ester and zinc glycinate.

The compositions according to the invention can comprise the esterase inhibitors in amounts of 0.01 to 20, preferably 0.1 to 10 and more particularly 0.5 to 5 wt.-%, based on the solids content of the composition.

The term "anti-bacterial agents" as used herein encompasses substances which have bactericidal and/or bacteriostatic properties. Typically these substances act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

In a preferred embodiment the antibacterial agent is selected from the group consisting of chitosan, phenoxyethanol, 5-Chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1, 2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.

The compositions according to the invention can comprise the antibacterial agents in amounts of 0.01 to 5 wt. % and preferably 0.1 to 2 wt.-%, based on the solids content of the composition.

The compounds of formula (I) as well as the mixtures of two or more compounds of formula (I), the stereoisomers thereof and the mixtures of stereoisomers thereof, as defined above, can be used in a wide range of aroma compositions. The olfactory properties, the substance properties (such as solubility in customary solvents and compatibility with further customary constituents of such compositions), as well as the toxicological acceptability of the compounds of formula (I) as well as the mixtures of two or more compounds of formula (I), the stereoisomers thereof and the mixtures of stereoisomers thereof underline their particular suitability for the stated use purposes and compositions.

Accordingly, in a preferred embodiment of the invention, the aroma chemical composition is an odor composition, more preferably a fragrance composition.

The composition according to the invention can be selected from, but is not limited to, the group consisting of perfume compositions, body care compositions, products for oral and dental hygiene, hygiene articles, cleaning compositions, textile detergent compositions, composition for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara.

Products for oral and dental hygiene include for example toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, polyols, surfactants, electrolytes, organic solvents or silicone derivatives.

The compounds of formula (I) as well as the mixtures of two or more compounds of formula (I), the stereoisomers thereof and the mixtures of stereoisomers thereof, as defined above, as well as the aroma chemical compositions according to the invention comprising them can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the compounds of formula (I) or the mixtures of two or more compounds of formula (I), or the stereoisomers thereof or mixtures of stereoisomers thereof, as defined above, and composition obtainable by the above method of the invention, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting the compounds of formula (I) or the mixtures of two or more compounds of formula (I), or the stereoisomers thereof or mixtures of stereoisomers thereof, as defined above, or the composition obtainable by the above method of the invention with a suitable wax-like substance and by extrusion with subsequent solidification, optionally in a suitable solvent, e.g. isopropanol.

Generally, the total amount of the compounds of formula (I) or the mixtures of two or more compounds of formula (I), or the stereoisomers thereof or mixtures of stereoisomers thereof, in the aroma chemical compositions according to the present invention is typically adapted to the particular intended use or the intended application and can, thus, vary over a wide range. As a rule, the customary standard commercial amounts for scents are used.

The compositions according to the invention can comprise the compounds of formula (I) or the mixtures of two or more compounds of formula (I), or the stereoisomers thereof or mixtures of stereoisomers thereof, as defined above, in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formula (I) or the mixtures of two or more compounds of formula (I), or the stereoisomers thereof or mixtures of stereoisomers thereof, as defined above, in an overall amount of from 0.001 to 5 weight %, preferably from 0.01 to 2 weight % based on the total weight of the composition.

A further aspect of the invention is directed to a method of preparing an aroma chemical composition, in particular a fragranced composition, especially a perfume composition, or for modifying the scent character of an aroma chemical composition, in particular of a fragranced composition, especially of a perfume composition, comprising incorporating a compound of formula (I) or a mixture of two or more compounds of the general formula (I) or a stereoisomer thereof or a mixture of two or more stereoisomers thereof, as defined above, into said composition.

In particular, the invention is directed to a method of preparing a perfume composition, body care composition, products for oral and dental hygiene, hygiene article, cleaning composition, textile detergent composition, compositions for scent dispensers, food, food supplement, pharmaceutical composition or crop protection composition, comprising including a compound of formula (I) or a mixture of two or more compounds of the general formula (I) or a stereoisomer thereof or a mixture of two or more stereoisomers thereof, as defined above, into said perfume composition, body care composition, products for oral and dental hygiene, hygiene article, cleaning composition, textile detergent composition, compositions for scent dispensers, food, food supplement, pharmaceutical composition or crop protection composition.

In one embodiment the invention is directed to a method for imparting a fruity, galbanum, camphorous, rooty and earthy note to a perfume composition, body care composition, products for oral and dental hygiene, hygiene article, cleaning composition, textile detergent composition, compositions for scent dispensers, food, food supplement, pharmaceutical composition or crop protection composition, which comprises including (1-ethyl-1,2-dimethyl-propyl) acetate in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting a fir needle, camphor, fresh, and natural note to a perfume composition, body care composition, products for oral and dental hygiene, hygiene article, cleaning composition, textile detergent composition, compositions for scent dispensers, food, food supplement, pharmaceutical composition or crop protection composition, which comprises including 1,1-diethylpropyl acetate in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting a floral, honey and dried fruit note to a perfume composition, body care composition, products for oral and dental hygiene, hygiene article, cleaning composition, textile detergent composition, compositions for scent dispensers, food, food supplement, pharmaceutical composition or crop protection composition, which comprises including a mixture comprising 70% by weight of 1,1-diethylallyl acetate and 25% by weight of 1,1-diethylpropyl acetate in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting a fruity, camphorous, sweet, cherry and solvent note to a perfume composition, body care composition, products for oral and dental hygiene, hygiene article, cleaning composition, textile detergent composition, compositions for scent dispensers, food, food supplement, pharmaceutical composition or crop protection composition, which comprises including 1,1-diethylpropyl propanoate in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting an ethereal, sweet, mouldy, hay, chocolate, *eucalyptus* and leafy note to a perfume composition, body care composition, products for oral and dental hygiene, hygiene article, cleaning composition, textile detergent composition, compositions for scent dispensers, food, food supplement, pharmaceutical composition or crop protection composition, which comprises including 3-methoxy-2,3-dimethyl-pentane in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting a mouldy, woody, cedarwood and galbanum note to a perfume composition, body care composition, products for oral and dental hygiene, hygiene article, cleaning composition, textile detergent composition, compositions for scent dispensers, food, food supplement, pharmaceutical composition or crop protection composition, which comprises including 3-ethyl-3-methoxy-pentane in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting a lovage, sweet, woody and fruity note to a perfume composition, body care composition, products for oral and dental hygiene, hygiene article, cleaning composition, textile detergent composition, compositions for scent dispensers, food, food supplement, pharmaceutical composition or crop protection composition, which comprises including a mixture comprising 85% by weight of (1-isopropyl-1-methyl-allyl) acetate and 10% by weight of (1-ethyl-1,2-dimethyl-propyl) acetate in a perfume composition, body care composition, products for oral and dental hygiene, hygiene article, cleaning composition, textile detergent composition, compositions for scent dispensers, food, food supplement, pharmaceutical composition or crop protection composition.

In another embodiment the invention is directed to a method for imparting an animalic, blackcurrant, sweet and technical note to a perfume composition, body care composition, products for oral and dental hygiene, hygiene article, cleaning composition, textile detergent composition, compositions for scent dispensers, food, food supplement, pharmaceutical composition or crop protection composition, which comprises including a mixture comprising 90% by weight of 3-ethyl-3-methoxypent-1-ene and 10% by weight of 3-ethyl-3-methoxy-pentane in a perfume composition, body care composition, products for oral and dental hygiene, hygiene article, cleaning composition, textile detergent composition, compositions for scent dispensers, food, food supplement, pharmaceutical composition or crop protection composition.

The compounds of the formula (I) can be prepared by standard methods of organic chemistry.

To be more precise, the compounds (I), where $R^4$ is selected from $C_1$-$C_4$-alkanoyl, can efficiently be prepared for example by reacting the alcohol of formula (II)

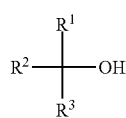

(II)

wherein $R^1$, $R^2$ and $R^3$ have one of the meanings given above,
with a $C_1$-$C_4$-carboxylic acid or a $C_1$-$C_4$-carboxylic acid anhydride in the presence of an esterification catalyst, or with a $C_1$-$C_4$-carboxylic acid chloride in the presence of a base.

Suitable esterification catalysts that can be applied in this reaction are well known to the skilled person. Suitable esterification catalysts are for example metal based catalysts, e.g. iron, cadmium, cobalt, lead, zinc, antimony, magnesium, titanium and tin catalysts in the form of metals, metal oxides or metal salts, such as metal alcoxylates; mineral acids, such as sulfuric acid, hydrochloric acid or phosphoric acid; or organic sulfonic acids, such as methane sulfonic acid or para-toluene sulfonic acid.

Suitable bases are preferably selected from organic bases. Suitable organic bases that can be used are for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

The individual reaction conditions for the preparation of the ester compounds of the general formula (I) are well known to the skilled person.

The compounds (I), where $R^4$ is selected from $C_1$-$C_4$-alkyl, can efficiently be prepared for example by reacting the alcohol of formula (II)

(II)

wherein $R^1$, $R^2$ and $R^3$ have one of the meanings given above,
with an alkylation reagent $R^4$—Y, wherein $R^4$ is selected from $C_1$-$C_4$-alkyl and Y represents a leaving group, selected from halogen, such as Cl, Br or I, sulfonates, such as tosylate, mesylate, triflate or nonaflate, sulfates, such as methylsulfate or ethylsulfate and carbonates, such as methylcarbonate or ethylcarbonatet, in the presence of a base.

Suitable bases are typically selected from inorganic bases and organic bases. Suitable inorganic bases that can be used in this alkylation reaction are for example alkali metal carbonates, e.g. $Li_2CO_3$, $Na_2CO_3$, $K_2CO_3$ or $Cs_2CO_3$, alkali metal hydroxides, e.g. LiOH, NaOH or KOH, and hydride donors, e.g. NaH, $LiAlH_4$ or $NaBH_4$.

Suitable organic bases that can be used in this alkylation reaction are for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

The alkylation reaction is performed under conventional alkylation reaction conditions that are well known to the skilled person.

The alcohol compounds (II) are either commercially available or they can be prepared from readily available precursors by using processes that are well described in the art.

For example, the alcohols of the general formula (II.a)

(II.a)

wherein R² and R³ have one of the meanings given above, can be prepared by ethynylation of the corresponding cycloketones of formula (III), as depicted in scheme 1 (step i)), followed by partial (selective) hydrogenation of the thus obtained acetylenically unsaturated alcohols (IV) (step ii)).

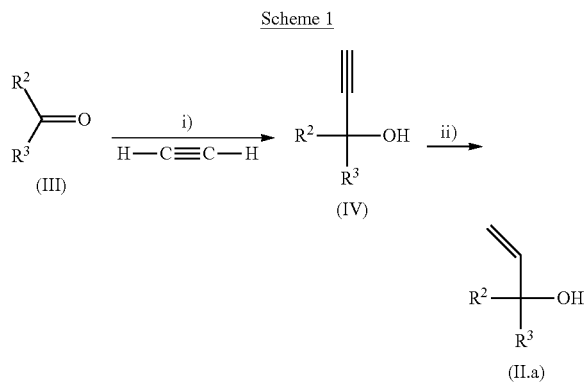

Scheme 1

Typically, step i) is carried out in the presence of a strong base, e.g. an alkali metal hydroxide, such as sodium hydroxide or potassium hydroxide, or an alkali metal alkoxide, such as potassium methoxide, sodium methoxide, potassium ethoxide, sodium ethoxide, potassium isopropoxide or sodium isopropoxide. The mineral base is usually applied in amounts ranging from 0.1 to 5 equivalents, based on the amount of the carbonyl compound (Ill). The ethynylation is typically carried out in the presence of an excess of acetylene (ethyne), i.e. at an acetylene pressure in the range of from 1 to 50 bar. Usually, the acetylene pressure is maintained at an appropriate value over the course of the ethynylation reaction.

The ethynylation is usually carried out in an inert solvent, i.e. a solvent that does not react with the starting materials, intermediates and reagents applied in the ethynylation or with the obtained products. Suitable solvents are for example alcohols, such as methanol, ethanol, propanol and isopropanol; aromatic and substituted aromatic hydrocarbons, such as benzene, chlorobenzene, dichlorobenzenes, toluene, xylene; and aliphatic hydrocarbons, such as pentane, hexanes, cyclohexane, heptanes, octanes, nonanes, decanes, ligroin and petrol ether, halogenated aliphatic hydrocarbons, such as dichloromethane, trichloromethane and tetrachloromethane, ethers, such as dibutyl ether, THF, 1,4-dioxane, 1,2-dimethoxyethane; as well as mixtures thereof.

A similar process, where the alkynylation reaction is performed in ammonia as the solvent while the strong base is only applied in catalytic amounts, is for example described in EP1532092 B1 and US2015/0246868 A1.

The partial (selective) hydrogenation in step ii) is typically carried out in liquid phase with hydrogen in the presence of a hydrogenation catalyst but can also be carried out in gas phase. Preferably, the partial (selective) hydrogenation in step ii) is carried out in liquid phase. The hydrogenation catalyst and the reaction conditions are chosen such that the carbon-carbon triple bond is only partially hydrogenated to the corresponding carbon-carbon double bond.

Suitable hydrogenation catalysts that can be applied in the partial hydrogenation of the triple bond of compounds (IV) are those customarily used in the hydrogenation of carbon-carbon triple bonds to carbon-carbon double bonds. The hydrogenation catalyst can be selected from homogeneous hydrogenation catalysts and heterogeneous hydrogenation catalysts. Preferably, the hydrogenation catalyst is selected from heterogeneous hydrogenation catalysts. If a heterogeneous hydrogenation catalyst is used in the partial (selective) hydrogenation in step ii), the heterogeneous hydrogenation catalyst is typically applied in the form of a granulate or a finely divided powder, or in the form of larger molded bodies, for example molded bodies having a defined particle size of one to several millimeters, e.g. 1, 2, 5 or 10 millimeters. If a heterogeneous hydrogenation catalyst is used, the partial (selective) hydrogenation in step ii) is preferably carried out in suspension mode or in fixed bed mode.

The heterogeneous hydrogenation catalysts preferably comprise at least one metal of group VIII. Suitable metals of group VIII are selected from the group consisting of ruthenium, cobalt, rhodium, nickel, palladium and platinum, preferably form the group consisting of ruthenium, nickel, palladium and platinum. The heterogeneous hydrogenation catalysts especially comprise palladium as the catalytically active species.

Furthermore, the heterogeneous hydrogenation catalysts that can be applied in the partial hydrogenation of the triple bond of compounds (IV) typically contain, in addition to the catalytically active metal, a catalyst poison, i.e. a substance, which reduces the activity/effectiveness of the catalyst, in order to prevent the further hydrogenation of the obtained olefinic species. Suitable catalyst poisons are for example metals other than the catalytically active metals, such as for example Sn, Pb, Zn, Cd, Sb or Bi; metal salts of inorganic anions, such as for example barium sulfate or calcium carbonate; inorganic compounds, such as CO, $CO_2$, $H_2O$, $H_2S$, $CS_2$, $SO_2$ or sulfur; or organic compounds, such as nitrogen containing heterocycles, e.g. quinoline and pyridine, or thiols, e.g. ethane thiol.

Preferably, the heterogeneous hydrogenation catalysts that can be applied in the partial hydrogenation of the triple bond of compounds (IV) are supported heterogeneous hydrogenation catalyst. The support may be any of a variety of materials on which a catalytically active material may be coated. Typically support materials are preferred, which have a rather high surface area and which are stable under the applied reaction and, if required, the applied regeneration conditions. Suitable materials are, for example, mineral materials, for example natural and synthetic minerals, metal oxides, glasses or ceramics, carbon, for example activated carbon or carbon black, plastics, for example synthetic or natural polymers, or combinations thereof. Preferred support materials are for example activated carbon, silicon dioxide, in particular amorphous silicon dioxide, alumina, titanium dioxide, chromium dioxide, and also the sulfates and carbonates of the alkaline earth metals, such as calcium carbonate, calcium sulfate, magnesium carbonate, magnesium sulfate, barium carbonate and barium sulfate. The supported heterogeneous hydrogenation catalyst may be used in the form of powders, particles, pellets, monoliths, honeycombs, packed beds, foams, aerogels, granules, beads, pills, cylinders, trilobes, extrudates, spheres or other rounded shapes, or in the form of other manufactured configurations.

The reaction temperature applied in the partial hydrogenation in step ii) is generally from 10 to 100° C., preferably from 15 to 70° C., in particular from 20 to 50° C. The hydrogen pressure is generally from 1 to 20 bar absolute (0.1 to 2 MPa), preferably from 1 to 10 bar absolute (0.1 to 1 MPa). The hydrogenation can be carried out in a variety of reactors known for this purpose, such as for example stirred tank reactors, fixed bed reactors and trickle bed reactors. Preference is given to fixed bed reactors or stirred tank reactors.

The hydrogenation reaction can be carried out in the presence or the absence of an inert solvent. Preferably, the hydrogenation reaction is carried carried out in the presence of an inert solvent. Suitable inert solvents are as defined above.

Similarly, the alcohols of the general formula (II.b)

wherein $R^2$ and $R^3$ have one of the meanings given above, can for example be prepared by ethynylation of the corresponding cycloketones of formula (III), as depicted in scheme 2 (step i)), followed by complete hydrogenation of the thus obtained acetylenically unsaturated alcohols (IV) (step iii)).

Scheme 2

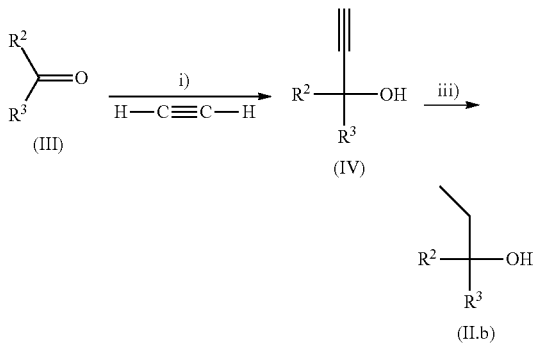

The catalytic hydrogenation in step iii) is typically carried out in liquid phase with hydrogen in the presence of a hydrogenation catalyst, but can also be carried out in gas phase. Preferably, the catalytic hydrogenation in step iii) is carried out in liquid phase.

Suitable hydrogenation catalysts are those customarily used in the hydrogenation of carbon-carbon triple bonds to carbon-carbon single bonds (complete hydrogenation). The hydrogenation catalyst can be selected from homogeneous hydrogenation catalysts and heterogeneous hydrogenation catalysts. Preferably, the hydrogenation catalyst is selected from heterogeneous hydrogenation catalysts. If a heterogeneous hydrogenation catalyst is used in the catalytic hydrogenation in step iii), the heterogeneous hydrogenation catalyst is typically applied in the form of a granulate or a finely divided powder, or in the form of larger molded bodies, as defined above. If a heterogeneous hydrogenation catalyst is used, the hydrogenation is preferably carried out in suspension mode or in fixed bed mode.

The hydrogenation catalysts preferably comprise at least one metal of group VIII and also VIIa. Suitable metals of group VIII are selected from the group consisting of iron, ruthenium, cobalt, rhodium, nickel, palladium and platinum. Particularly suitable metals of group VIII are iron, ruthenium, nickel, palladium and platinum. A suitable metal of group VIIa is rhenium. The metals may also be used in the form of mixtures, for example two or more metals of the group VIII. Metals of group VIII may also comprise further metals, for example metals of group VIIa, in particular rhenium, or metals of group Ib, i.e. copper, silver or gold. The catalyst especially comprises palladium as the catalytically active species.

The heterogeneous hydrogenation catalysts applied in the catalytic hydrogenation in step iii) can be supported or unsupported. Preferably, the heterogeneous hydrogenation catalysts applied in the catalytic hydrogenation in step iii) is a supported heterogeneous hydrogenation catalyst. Suitable supports are as defined above.

When a heterogeneous catalyst is used, it is preferably present in finely divided form, i.e. in the form of a fine granulate or a finely divided powder. The finely divided form is achieved, for example, as follows:
  a) Black catalyst: shortly before use as a catalyst, the metal is deposited reductively from the solution of one of its salts.
  b) Adams catalyst: the metal oxides, in particular the oxides of platinum and palladium, are reduced in situ by the hydrogen used for the hydrogenation.
  c) Skeletal or Raney catalyst: the catalyst is prepared as a "metal sponge" from a binary alloy of the metal (in particular nickel or cobalt) with aluminum or silicon by leaching out one partner with acid or alkali. Residues of the original alloy partner often act synergistically.
  d) Supported catalyst: black catalysts can also be precipitated on the surface of a support substance. Suitable supports and support materials are described below.

The reaction temperature is generally from 10 to 100° C., preferably from 15 to 70° C., in particular from 20 to 50° C. The hydrogen pressure is generally from 2 to 100 bar absolute (0.2 to 10 MPa), preferably from 5 to 50 bar absolute (0.5 to 5 MPa). The hydrogenation can be carried out in a variety of reactors known for this purpose. Preference is given to fixed bed reactors, in particular to trickle bed reactors.

The catalytic hydrogenation reaction in step iii) can be carried carried out in the presence or the absence of an inert solvent. Preferably, the hydrogenation reaction is carried carried out in the presence of an inert solvent. Suitable inert solvents are as defined above.

Generally, the reaction mixtures are worked up in a customary manner, for example by mixing with water, neutralizing the reaction mixture, if acids and bases were applied in the reaction, separating the phases, isolating the product from the organic phases and, if appropriate, purifying the crude products by usual methods, e.g. by distillative, extractive or chromatographic methods. If the reaction is not run in fixed bed mode and a heterogeneous catalyst, e.g. a heterogeneous hydrogenation catalyst, is applied in the reactions the catalyst is filtered off prior to work up.

In another aspect, the invention relates to a compound of the general formula (I.a) or a stereoisomer thereof

wherein
R² is C₁-C₃-alkyl,
R³ is C₂-C₄-alkyl and
R⁴ᵃ is C₂-C₄-alkyl,
except for the compounds 3-ethoxy-3-ethyl-hexane, 3-ethoxy-3-methyl-pentane and 3-ethoxy-3-ethyl-pentane,
or
a compound of the general formula (I.b) or a stereoisomer thereof

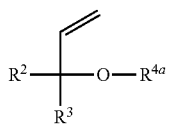

(I.b)

wherein
R² is C₁-C₃-alkyl,
R³ is C₂-C₄-alkyl and
R⁴ᵃ is C₂-C₄-alkyl,
except for the compounds 3-ethoxy-3-methylhept-1-ene and 3-ethoxy-3-methylpent-1-ene.

Preferably, in these compounds (I.a) and (I.b) R² is methyl or ethyl.

Preferably, in these compounds (I.a) and (I.b) R³ is ethyl, n-propyl, isopropyl or n-butyl, more preferably ethyl, n-propyl or isopropyl, in particular ethyl or isopropyl, especially isopropyl.

Preferably, in these compounds (I.a) and (I.b) R⁴ᵃ is C₂-C₃-alkyl, in particular ethyl.

In particular, the invention relates to 3-ethoxy-2,3-dimethyl-pentane.

The compounds of the general formulae (I.a) and (I.b) can be prepared as described above for the ether compounds of the general formula (I).

Accordingly, the present invention also relates to a method for preparing a compound of formulae (I.a) or (I.b) or a mixture of two or more compounds of formulae (I.a) and/or (I.b) or a stereoisomer thereof or a mixture of stereoisomers thereof, as defined above, comprising the following steps:
(i) providing a ketone of formula (III), wherein R² is C₁-C₃-alkyl and R³ is C₂-C₄-alkyl,
(ii) reacting the ketone provided in step (i) with acetylene in the presence of a base to obtain an acetylenically unsaturated alcohol of the general formula (IV), wherein R² is C₁-C₃-alkyl and R³ is C₂-C₄-alkyl,
(iii) partially or completely hydrogenating the acetylenically unsaturated alcohol (IV) obtained in step (ii) with hydrogen in the presence of a hydrogenation catalyst to obtain the saturated alcohol of the general formula (II.a), wherein R² is C₁-C₃-alkyl and R³ is C₂-C₄-alkyl (complete hydrogenation), or the olefinic alcohol of the general formula (II.b), wherein R² is C₁-C₃-alkyl and R³ is C₂-C₄-alkyl (partial hydrogenation),
(iv) reacting the alcohol (II.a) or (II.b) obtained in step (iii) with an alkylation reagent R⁴ᵃ—Y, wherein R⁴ᵃ is C₂-C₄-alkyl and Y represents a leaving group, selected from halogen, such as Cl, Br or I, sulfonates, such as tosylate, mesylate, triflate or nonaflate, sulfates, such as methylsulfate or ethylsulfate and carbonates, such as methylcarbonate or ethylcarbonatet, in the presence of a base, to obtain a raw-product mixture, and
(v) subjecting the raw-product mixture obtained in step (iv) to a purification step.

Suitable and preferred reagents and reaction conditions as well as preferred meanings of R², R³ and R⁴ᵃ are as described above.

The invention is illustrated by the following examples.

EXAMPLES

Abbreviations

GC: Gas Chromatography
RT: retention time
DMAP: 4-dimethylaminopyridine
MTBE: methyl tert.-butyl ether Analytics The purity of the products was determined by gas chromatography on the basis of area-%:
GC-system: Agilent 7890 B;
GC-Column: DB-WAX (30 m (Length), 0.32 mm (ID), 0.25 micrometer (film));
Temperature program: 85° C. to 230° C. at 5°/min
The products were identified by ¹³C NMR.

1. Preparation Examples 1.1 Preparation of 3,4-dimethylpent-1-yn-3-ol

In a 5 l autoclave, 308.5 g (5.5 mol) sodium methoxide is suspended in 1500 ml tetrahydrofurane and purged with nitrogen. The autoclave is pressurized with 2 bar nitrogen and 18 bar acetylene at 10° C. 5 mol of 3-methyl-2-butanone is continuously added over 16 h at 10° C., while keeping the pressure at 20 bar. The mixture is stirred for additional 5 h at 0° C. before releasing the pressure. 500 ml water is carefully added while keeping the temperature below 30° C. The organic phase is separated, the pH adjusted to pH7 with phosphoric acid and the so obtained crude product is fractionated distilled to obtain the pure 3,4-dimethylpent-1-yn-3-ol.

1.2 Preparation of 2,3-dimethylpentane-3-ol

A Steel-Autoclave was charged with 25 g of the 3,4-dimethylpent-1-yn-3-ol obtained in example 1.1 and 50 ml of methanol. 2 g of catalyst (5% Pd/C) was added and the hydrogenation was performed at 30 bar hydrogen pressure and 60° C. After complete conversion (checked by GC), the reaction was stopped, the catalyst was filtered over celite and the solvent was evaporated. The crude product, i.e. 2,3-dimethylpentane-3-ol was directly used in the following step.

1.3 Preparation of 3-ethylpent-1-yn-3-ol

In a 5 l autoclave, 308.5 g (5.5 mol) sodium methoxide is suspended in 1500 ml tetrahydrofurane and purged with nitrogen. The autoclave is pressurized with 2 bar nitrogen and 18 bar acetylene at 10° C. 5 mol of 3-pentanone is continuously added over 16 h at 10° C., while keeping the pressure at 20 bar. The mixture is stirred for additional 5 h at 0° C. before releasing the pressure. 500 ml water is carefully added while keeping the temperature below 30° C. The organic phase is separated, the pH adjusted to pH7 with phosphoric acid and the so obtained crude product is fractionated distilled to obtain the pure 3-ethylpent-1-yn-3-ol.

1.4 Preparation of 3-ethylpent-1-en-3-ol

An Steel-Autoklave was charged with 24.8 g of 13-ethylpent-1-yn-3-ol, 125 g methanol and 0.15 g Lindlar-Catalyst (Pd on Calcium Carbonat, Poisoned with lead, commercially available e.g. from Sigma-Aldrich). The Hydrogenation was performed at a hydrogen pressure of 4 bar and a temperature of 25° C. After a reaction time of 20 min. complete conversion of the starting material was observed. The partial hydrogenation was observed with a selectivity of 80% (GC area-%).

The reaction was stopped. The catalyst was filtered off and the solvent was evaporated at reduced pressure. The reaction product, i.e. a mixture of 3-ethylpent-1-en3-ol with 3-ethylpentane-3-ol, was directly applied in the next step without further purification.

1.5 Preparation of 3-ethylpentane-3-ol

A Steel-Autoclave was charged with 25 g of the 3-ethylpent-1-yn-3-ol obtained in example 1.3 and 50 ml of methanol. 2 g of catalyst (5% Pd/C) was added and the hydrogenation was performed at 30 bar hydrogen pressure and 80° C. After complete conversion (check by GC), the reaction was stopped, the catalyst was filtered over celite and the solvent was evaporated. The crude product, i.e. 3-ethylpentane-3-ol, was directly applied in the following step.

1.6 Preparation of (1-ethyl-1,2-dimethyl-propy) acetate

| Compound | MW | Mass/Volume | Moles |
| --- | --- | --- | --- |
| 2,3-dimethylpentane-3-ol | 116.20 | 15 g | 0.129 |
| acetic anhydride | 102.09 | 15.81 g | 0.155 |
| N,N'-dimethylaminopyridine | 122.17 | 0.473 g | 0.004 |
| Tetrahydrofuran |  | 50 mL |  |

DMAP was added to the THF solution of the alcohol at RT. The mixture was set to reflux (53° C.) and acetic anhydride (1.2 eq) was slowly added at this temperature. After 23 h, 63% alcohol conversion was observed by GC. The reaction was cooled down to room temperature and slowly quenched with 50 mL of water. 50 mL of ethyl acetate were then added. The organic phase was separated and washed with NaHCO₃ and brine solution. The organic extracts were combined and dried with sodium sulfate. After evaporating the solvent at reduced pressure, 20.4 g of crude product that contained ca 52% of the acetate according to the GC (area %) were obtained. The product was purified by column chromatography. The corresponding acetate was obtained with a purity of 99% (GC area %). The identity of the product was confirmed by NMR.

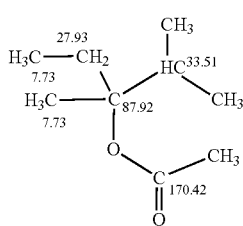

(1-Ethyl-1,2-dimethylpropyl) acetate: $^{13}$C NMR (125 MHz, CDCl$_3$): δ=7.73, 16.96, 17.08, 22.03, 27.93, 33.51, 87.92, 170.42

1.7 Preparation of 1,1-diethylpropyl acetate

| Compound | MW | Mass/Volume | Moles |
| --- | --- | --- | --- |
| 3-ethyl-3-pentanol | 116.20 | 15 g | 0.129 |
| acetic anhydride | 102.09 | 15.81 g | 0.155 |
| N,N'-dimethylaminopyridine | 122.17 | 0.473 g | 0.004 |
| Tetrahydrofuran |  | 70 mL |  |

DMAP was added to the THF solution of 3-ethyl-3-pentanol at RT. The mixture was set to reflux (53° C.) and acetic anhydride (1.2 eq) was slowly added at this temperature. After 167 h, 93% alcohol conversion was observed by GC. The reaction was cooled down to room temperature and slowly quenched with 50 mL of water. 50 mL of ethyl acetate were then added. The organic phase was separated and washed with NaHCO₃ and brine solution. The organic extracts were combined and dried with sodium sulfate. After evaporating the solvent at reduced pressure, 17.6 g of crude product that contained ca 89% of the acetate according to the GC (area %) were obtained. The product was purified by column chromatography. The corresponding acetate was obtained with a purity of 99% (GC area %). The identity of the product was confirmed by NMR.

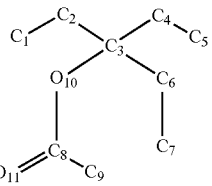

1,1-Diethylpropyl acetate: $^{13}$C NMR (125 MHz, CDCl$_3$): δ=7.70 (C1/C5/C7), 22.17 (C9), 26.58 (C2/C4/C6), 88.12 (C3), 170.22 (C8)

1.8 Preparation of 1,1-diethylallyl acetate

| Compound | MW | Mass/Volume | Moles |
| --- | --- | --- | --- |
| Mixture of 3-ethylpent-1-en-3-ol and 3-ethylpentane-3-ol | 114.19 | 10 g | 0.088 |
| acetic anhydride | 102.09 | 10.72 g | 0.105 |
| N,N'-dimethylaminopyridine | 122.17 | 0.321 g | 0.003 |
| Tetrahydrofuran |  | 50 mL |  |

DMAP was added to the THF solution of a mixture of 3-ethylpent-1-en-3-ol and 3-ethylpentane-3-ol, obtained in example 1.4, at RT. The mixture was set to reflux (53° C.) and acetic anhydride (1.2 eq) was slowly added at this temperature. After 71 h, the reaction was cooled down to room temperature and slowly quenched with 50 mL of water. 50 mL of ethyl acetate were then added. The organic phase was separated and washed with NaHCO₃ and brine solution. The organic extracts were combined and dried with sodium sulfate. After evaporating the solvent at reduced pressure, 9.6 g of crude product that contained ca. 30% of the acetate according to the GC (GC area-%) together with ca. 40% of compound 1,1-diethylpropyl acetate were obtained. The product was purified by column chromatography. The corresponding acetate was evaluated with a purity of 70% (GC area-%) in a mixture with 25% of 1,1-diethylpropyl acetate. The identity of the product was confirmed by NMR.

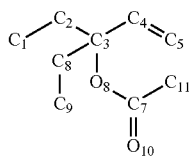

1,1-Diethylallyl acetate: $^{13}$C NMR (125 MHz, CDCl$_3$): δ=6.50 (C1/C9), 20.91 (C11), 27.63 (C2/C8), 85.35 (C3), 112.93 (C5), 139.30 (C4), 169.23 (C7)

1.9 Preparation of 1,1-diethylpropyl propanoate

| Compound | MW | Mass/Volume | Moles |
|---|---|---|---|
| 3-ethyl-3-pentanol | 116.20 | 15 g | 0.129 |
| propionic anhydride | 130.14 | 21.84 g | 0.168 |
| N,N'-dimethylaminopyridine | 122.17 | 0.473 g | 0.004 |
| Tetrahydrofuran | | 70 mL | |

DMAP was added to the THF solution of the alcohol at RT. The mixture was set to reflux (53° C.) and propionic anhydride (1.2 eq) was slowly added at this temperature. After 23 h, ca. 70% alcohol conversion was observed by GC. The reaction was cooled down to room temperature and slowly quenched with 50 mL of water. 50 mL of ethyl acetate were then added. The organic phase was separated and washed with NaHCO$_3$ and brine solution. The organic extracts were combined and dried with sodium sulfate. After evaporating the solvent at reduced pressure, 22 g of crude product that contained ca 50% of the propionate according to the GC (area %) were obtained. The product was purified by column chromatography. The corresponding propioinate was obtained with a purity >98% (GC area %). The identity of the product was confirmed by NMR.

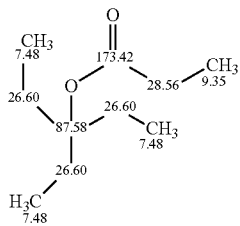

1,1-Diethylpropyl propionate: $^{13}$C NMR (125 MHz, CDCl$_3$): δ=7.48, 9.35, 26.60, 28.56, 87.58, 173.42

1.10 Preparation of 3-methoxy-2,3-dimethylpentane

| Compound | MW | Mass/Volume | Moles |
|---|---|---|---|
| 2,3-dimethylpentan-3-ol | 116.20 | 10 g | 0.086 |
| Methyl Iodide | 141.94 | 15.9 g | 0.112 |
| Sodium hydride | 23.99 | 2.7 g | 0.112 |
| THF | | 105 mL | |

To a dispersion of sodium hydride (1.3 eq) in 75 mL of THF a solution of 2,3-dimethylpentan-3-ol in 30 mL of THF was slowly added at 0° C. The mixture was stirred 30 min at 0° C. After this time, 1.3 eq of methyl iodide were slowly added at RT. After the addition, the mixture was stirred at 40° C. for 4.5 h. After this time, the reaction mixture was cooled down to 0° C. and the addition of 0.25 eq of NaH followed by 0.25 eq of methyl iodide was repeated. The mixture was then stirred for 18 h at 40° C. At this point, the reaction was slowly quenched with 50 mL of water. The organic phase was extracted with 3 times 50 mL MTBE. The organic extracts were combined and washed with 50 mL of NH$_3$ solution and with 50 mL brine solution. The organic extracts were combined and dried with sodium sulfate. After evaporating the solvent at reduced pressure 11.3 g of crude product were obtained with 99% of the methyl ether derivative according to the GC (area-%). The product was purified by distillation. The corresponding ether was obtained with a purity 99%. The identity of the product was confirmed by NMR.

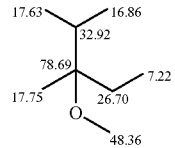

3-Methoxy-2,3-dimethyl-pentane: $^{13}$C NMR (125 MHz, CDCl$_3$): δ=7.22, 16.86, 17.63, 17.75, 26.70, 32.92, 48.36, 78.69.

1.11 Preparation of 3-ethyl-3-methoxy-pentane

| Compound | MW | Mass/Volume | Moles |
|---|---|---|---|
| 3-ethyl-3-pentanol | 116.20 | 10 g | 0.086 |
| Methyl Iodide | 141.94 | 15.9 g | 0.112 |
| Sodium hydride | 23.99 | 2.7 g | 0.112 |
| THF | | 105 mL | |

To a dispersion of sodium hydride (1.3 eq) in 75 mL of THF a solution of 3-ethyl-3-pentanol in 30 mL of THF was slowly added at 0° C. The mixture was stirred 30 min at 0° C. After this time, 1.3 eq of methyl iodide were slowly added at RT. After the addition, the mixture was stirred at 40° C. for 4 h. After this time, the reaction mixture was cooled down to 0° C. and the addition of 0.25 eq of NaH followed by 0.25 eq of methyl iodide was repeated. The mixture was then stirred for 18 h at 40° C. At this point, the reaction was slowly quenched with 50 mL of water. The organic phase was extracted with 3 times 50 mL MTBE. The organic extracts were combined and washed with 50 mL of NH$_3$ solution and with 50 mL brine solution. The organic extracts were combined and dried with sodium sulfate. After evaporating the solvent at reduced pressure 8 g of crude product were obtained with 99% of the methyl ether derivative according to the GC (area-%). The product was purified by distillation. The corresponding ether was obtained with a purity >99%. The identity of the product was confirmed by NMR.

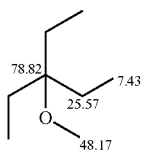

3-Ethyl-3-methoxy-pentane: $^{13}C$ NMR (125 MHz, CDCl$_3$): δ=7.43, 25.57, 48.14, 78.82.

1.12 Preparation of (1-isopropyl-1-methyl-allyl) acetate

| Compound | MW | Mass/Volume | Moles |
| --- | --- | --- | --- |
| Mixture of 3,4-dimethylpent-1-en-3-ol and 2,3-dimethyl-pentan-3-ol | 114.19 | 15 g | 0.131 |
| acetic anhydride | 102.09 | 16.1 g | 0.158 |
| N,N'-dimethylaminopyridine | 122.17 | 0.481 g | 0.004 |
| Tetrahydrofuran | | 50 mL | |

DMAP was added to the THF solution of a mixture of 3,4-dimethylpent-1-en-3-ol and 2,3-dimethylpentan-3-ol (82:10), at RT. The mixture was set to reflux (53° C.) and acetic anhydride (1.2 eq) was slowly added at this temperature. After 23 h, the reaction was cooled down to room temperature and slowly quenched with 50 mL of water. 50 mL of ethyl acetate were then added. The organic phase was separated and washed with NaHCO$_3$ and brine solution. The organic extracts were combined and dried with sodium sulfate. After evaporating the solvent at reduced pressure, 13.5 g of crude product that contained ca. 42% of the acetate according to the GC (GC area-%). The product was purified by column chromatography. The corresponding acetate was evaluated with a purity of 80% (GC area-%) in a mixture with 10% of (1-ethyl-1,2-dimethyl-propyl) acetate. The identity of the product was confirmed by NMR.

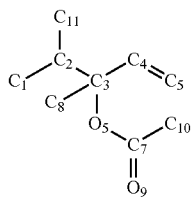

1-Isopropyl-1-methyl-allyl) acetate: $^{13}C$ NMR (125 MHz, CDCl$_3$): δ=16.94 (C11), 17.10 (C1), 19.33 (C8), 22.22 (C10), 36.28 (C2), 85.84 (C3), 114.12 (C5), 140.10 (C4), 169.98 (C7).

1.13 Preparation of 3-ethyl-3-methoxy-pent-1-ene

| Compound | MW | Mass/Volume | Moles |
| --- | --- | --- | --- |
| Mixture of 3-ethyl-pent-1-en-3-ol and 3-ethyl-3-pentanol | 114.19 | 10 g | 0.088 |
| Methyl iodide | 141.94 | 16.2 g | 0.114 |
| Sodium hydride | 23.99 | 2.7 g | 0.114 |
| THF | | 105 mL | |

To a dispersion of sodium hydride (1.3 eq) in 75 mL of THF a solution of a mixture of 3-ethylpent-1-en-3-ol and 3-ethyl-3-pentanol (80:20) in 30 mL of THF was slowly added at 0° C. The mixture was stirred 30 min at 0° C. After this time 1.3 eq of methyl iodide were slowly added at RT. After the addition, the mixture was stirred at 40° C. for 4 h. After this time, the reaction mixture was cooled down to 0° C. and the addition of 0.25 eq of NaH followed by 0.25 eq of methyl iodide was repeated. The mixture was then stirred for 18 h at 40° C. At this point, the reaction was slowly quenched with 50 mL of water. The organic phase was extracted with 3 times 50 mL MTBE. The organic extracts were combined and washed with 50 mL of NH$_3$ solution and with 50 mL brine solution. The organic extracts were combined and dried with sodium sulfate. After evaporating the solvent at reduced pressure 8 g of crude product were obtained with ca. 70% of the methyl ether derivative according to the GC (area-%). The product was purified by column chromatography. The corresponding methyl ether was evaluated with a purity of 90% (GC area-%) in a mixture with 10% of 3-ethyl-3-methoxy-pentane. The identity of the product was confirmed by NMR.

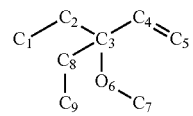

3-ethyl-3-methoxy-pent-1-ene: 13C NMR (125 MHz, CDCl$_3$): δ=7.41 (C1, C9), 26.51 (C2, C8), 49.41 (C7), 79.75 (C3), 115.42 (C5), 142.04 (C4).

2. Olfactory Assessment

In order to test the quality and intensity of the odor of the compounds (I) of the present invention, scent strip tests were performed.

For this purpose, strips of absorbent paper were dipped into solution containing 1 to 10% by weight solution of the compound (1) to be tested in ethanol. After evaporation of the solvent (about 30 sec.) the scent impression was olfactively evaluated by a trained perfumer.

The results of the scent test are summarized in table 1.

TABLE 1

Results of the scent tests.

| Example no. | Compound | Description |
|---|---|---|
| 1.6 | 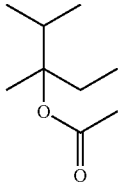 | Fruity, galbanum, camphorous, rooty, earthy |
| 1.7 | 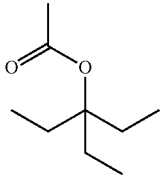 | Fir needle, Camphor, Fresh, Natural |
| 1.8 | 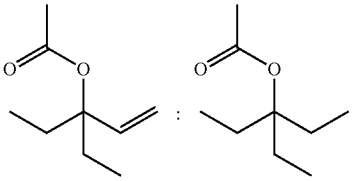 70:25 | Floral, honey, dried fruit |
| 1.9 |  | Fruity, camphorous, sweet, cherry, solvent |
| 1.10 | 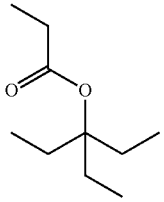 | Ethereal, sweet, mouldy, hay, chocolate, eucalyptus, leafy |
| 1.11 | 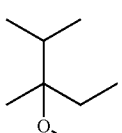 | Mouldy, woody, cedarwood, galbanum |
| 1.12 | 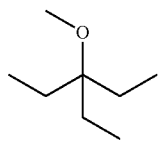 85:10 | Lovage, sweet, woody, fruity |

TABLE 1-continued

Results of the scent tests.

| Example no. | Compound | Description |
|---|---|---|
| 1.13 | 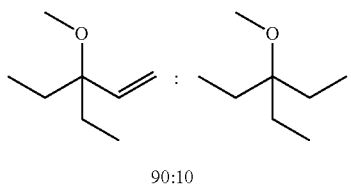<br>90:10 | Animalic, blackcurrant, sweet, technical |

The invention claimed is:

1. An aroma chemical composition comprising
a compound of formula (I) or a mixture of two or more compounds of the general formula (I) or a stereoisomer thereof or a mixture of two or more stereoisomers thereof as an aroma chemical ingredient,

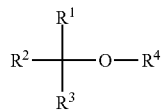 (I)

wherein
$R^1$ is ethyl or ethenyl,
$R^2$ is $C_1$-$C_3$-alkyl,
$R^3$ is $C_2$-$C_3$-alkyl and
$R^4$ is $C_1$-$C_4$-alkyl,
and
at least one additional aroma chemical, a non-aroma chemical carrier, and mixtures thereof, where the non-aroma chemical carrier is selected from the group consisting of surfactants, oil components and solvents; where the solvents are selected from the group consisting of ethanol, isopropanol, diethylene glycol monoethyl ether, glycerol, propylene glycol, 1,2-butylene glycol, dipropylene glycol, triethyl citrate, diethyl phthalate, isopropyl myristate and benzyl benzoate.

2. The composition according to claim 1, wherein the composition is selected from the group consisting of perfume compositions, body care compositions, products for oral and dental hygiene, hygiene articles, cleaning compositions, textile detergent compositions, compositions for scent dispensers, foods, food supplements, pharmaceutical compositions and crop protection compositions.

3. The composition according to claim 1, where $R^1$ is ethyl.

4. The composition according to claim 1, where $R^2$ is methyl or ethyl.

5. The composition according to claim 1, where $R^4$ is methyl or ethyl.

6. The composition according to claim 1, comprising of the mixture of two or more compounds of formula (I).

7. A process for modifying a scent of a fragranced composition which comprises utilizing the aroma chemical composition of claim 1 in the fragranced composition.

8. A method of preparing a scent of a fragranced composition comprising incorporating the aroma chemical composition of claim 1 into the fragranced composition.

* * * * *

UNITED STATES PATENT AND TRADEMARK OFFICE
CERTIFICATE OF CORRECTION

PATENT NO. : 12,291,690 B2
APPLICATION NO. : 17/286338
DATED : May 6, 2025
INVENTOR(S) : Christoph Stock et al.

Page 1 of 1

It is certified that error appears in the above-identified patent and that said Letters Patent is hereby corrected as shown below:

In the Claims

Claim 29, Column 45, Lines 36 and 37, change "at least one additional aroma chemical, a non-aroma chemical carrier, and mixtures thereof," to --at least one additional aroma chemical, a non-aroma chemical carrier, or mixtures thereof,--.

Signed and Sealed this
Twenty-sixth Day of August, 2025

Coke Morgan Stewart
*Acting Director of the United States Patent and Trademark Office*